United States Patent [19]
Bisera et al.

[11] 4,345,594
[45] Aug. 24, 1982

[54] CLOSELY CONTROLLABLE INTRAVENOUS INJECTION SYSTEM

[75] Inventors: Jose Bisera, Camarillo; Max H. Weil, Beverly Hills, both of Calif.

[73] Assignee: Institute of Critical Care Medicine, Los Angeles, Calif.

[21] Appl. No.: 186,681

[22] Filed: Sep. 12, 1980

[51] Int. Cl.³ .............................................. A61M 5/00
[52] U.S. Cl. ........................ 128/214 F; 128/DIG. 12; 417/543
[58] Field of Search ........... 128/214 R, 214 E, 214 F, 128/214.2, DIG. 12, DIG. 13, DIG. 3; 417/383, 394, 395, 478, 479, 543

[56] References Cited

U.S. PATENT DOCUMENTS

| | | | |
|---|---|---|---|
| 2,812,716 | 11/1957 | Gray | 417/389 |
| 2,832,294 | 4/1958 | Rippingille | 417/543 X |
| 3,007,416 | 11/1961 | Childs | 417/479 |
| 3,048,121 | 8/1962 | Sheesley | 417/394 |
| 3,075,524 | 1/1963 | Clark | 128/DIG. 3 |
| 3,099,260 | 7/1963 | Birtwell | 128/1 D |
| 3,551,076 | 12/1970 | Wilson | 417/478 X |
| 3,814,547 | 6/1974 | Kitrilakis et al. | 417/383 |
| 3,883,272 | 5/1973 | Puckett | 417/383 |
| 3,951,572 | 4/1976 | Ray, Jr. et al. | 417/389 |
| 4,043,332 | 8/1977 | Metcalf | 128/214 E |
| 4,155,362 | 5/1979 | Jess | 128/214 F |

OTHER PUBLICATIONS
Lancet, Aug. 3, 1963, p. 228.

Primary Examiner—Dalton L. Truluck
Attorney, Agent, or Firm—Freilich, Hornbaker, Wasserman, Rosen & Fernandez

[57] ABSTRACT

An apparatus is provided for injecting fluid into a patient over an extended period of time, such as in intravenous feeding of a patient. The apparatus enables close control of injection quantity and rate while assuring an even flow into the patient. The apparatus utilizes relatively simple disposable parts. The apparatus includes an air-operated peristaltic pump which pumps a controlled amount of fluid in each cycle of operation, and a pressure moderator which receives the liquid pulses and supplies an even flow to the patient. The moderator includes a closed chamber, and a resilient tube connected to the pump and having slits that permit the escape of pumped liquid into the chamber. The peristaltic pump includes a flexible but nonresilient tube connected to the container, the nonelasticity assuring that the tube does not expand beyond a predetermined dimension when a vacuum is applied to it.

4 Claims, 3 Drawing Figures

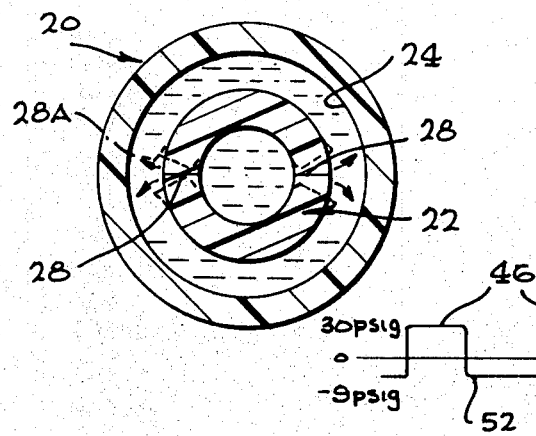
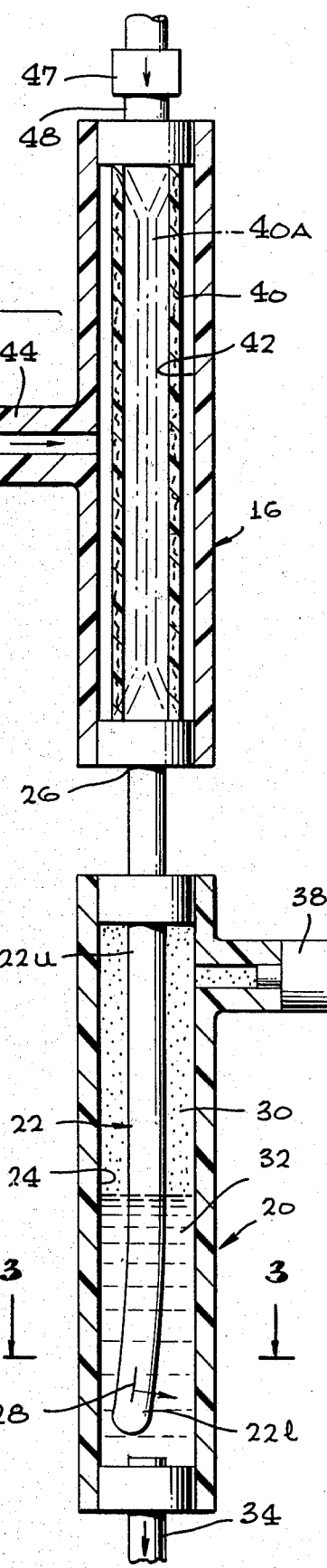
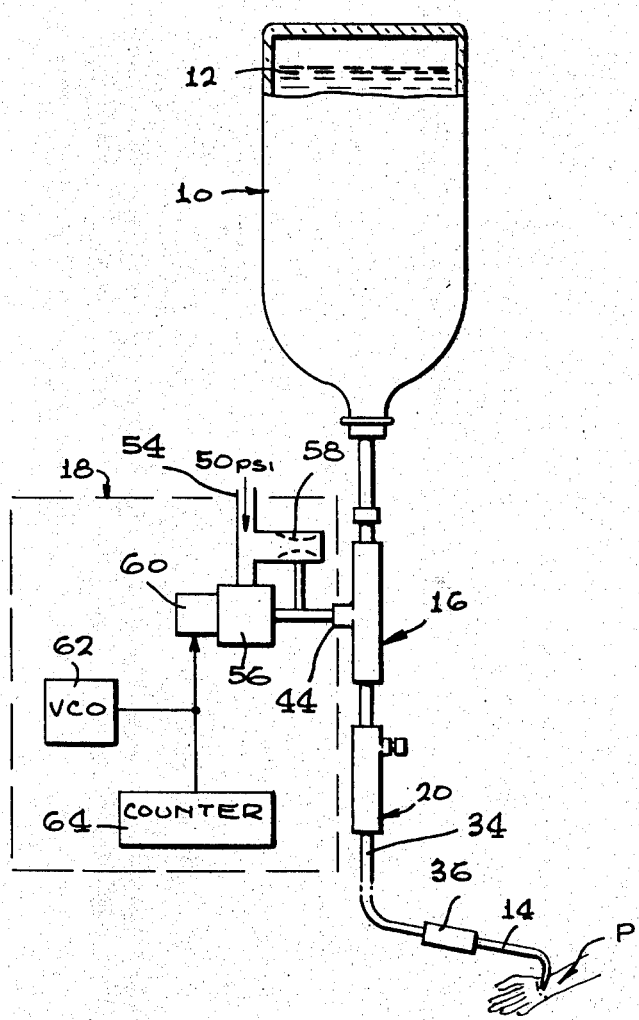

CLOSELY CONTROLLABLE INTRAVENOUS INJECTION SYSTEM

BACKGROUND OF THE INVENTION

A common set-up for the administration of intravenous fluids to a patient, such as saline solution to which medication may have been added, includes a drip chamber connected to a catheter which extends to the patient. A valve below the drop chamber controls the rate of administration of the fluid to the patient. In some situations, such as in critical care environments, it may be necessary to closely control the rate at which fluid is administered to the patient over an extended period of time. While the common set-up involves simple disposable items, it does not permit close control of the rate of administration of the fluid to the patient. An apparatus which enables the administration of fluid over an extended period of time, wherein the parts which contacted the fluid were of low cost to permit them to be disposable, would be of considerable value. In such an apparatus, any power required to operate it should be derived primarily from pressured air which is commonly available in a hospital and which avoids the possibility of electrical shocks from electric power outlets.

SUMMARY OF THE INVENTION

In accordance with one embodiment of the present invention, an apparatus is provided for closely controlling the administration of fluid into a patient over an extended time period, using relatively low cost and disposable sterile parts, which enables close control of volumetric fluid flow while assuring a relatively even flow of the fluid to the patient. The apparatus includes a peristaltic pump operated by air pulses, and a pressure moderator located between the outlet of the pump and a catheter which extends to the patient. The pressure moderator includes a resilient tube having a closed end lying in a sealed chamber, and with at least one slit in the tube. Fluid pulses flowing into the tube exit through the slit to raise the level of fluid in the chamber, and thereby compress gas in the chamber to push out fluid through an opening to flow through the catheter to the patient.

The peristaltic pump may be of the type which utilizes pressure pulses to collapse a flexible tube, to thereby pump fluid out of the tube. In order to closely control the amount of fluid pumped in each cycle of operation, a flexible but nonresilient pump tube is utilized, so that the tube does not expand beyond a predetermined configuration when filled. In order to assure rapid filling of the tube despite its supply from a container at a low pressure head, a vacuum is applied around the flexible but nonelastic pump tube to rapidly expand it after each pressure pulse.

The novel features of the invention are set forth with particularity in the appended claims. The invention will best be understood from the following description when read in conjunction with the accompanying drawings.

BRIEF DESCRIPTION OF THE DRAWINGS

FIG. 1 is a side elevation view of an injection system constructed in accordance with one embodiment of the present invention;

FIG. 2 is a partial sectional view of the system of FIG. 1;

FIG. 3 is a view taken on the line 3—3 of FIG. 2.

DESCRIPTION OF THE PREFERRED EMBODIMENT

FIG. 1 illustrates an intravenous administration system which includes a container 10 holding a fluid 12 to be administered such as a saline solution to which a medication may have been added, and which is to be administered through a catheter 14 having a needle inserted into the vein of a patient P. The system includes a pump 16 operated in a closely controlled fashion by a controller 18, to move the fluid from the container to the catheter at a closely controlled rate. In modern medical practice, items that directly contact fluid administered to a patient are usually designed to be disposable and sterile, thus avoiding the need for re-sterilization. To this end, the pump 16 is of the peristaltic type, wherein a flexible tube carrying the fluid is repeatedly compressed and released to pump the fluid from the container 10 towards the catheter 14. While the peristaltic pump 16 enables the use of low cost disposable items in contact with the fluid to be administered, it has the disadvantage of moving the fluid in pulses towards the catheter 14. In intravenous feeding or administration of medication to the patient, it is normally desirable to provide a relatively even flow of fluid into the patient's vein. It should be noted that since only liquids are normally administered over an extended period to a patient and the term "fluid" herein refers to liquids.

The pulses produced by the peristaltic pump 16 are moderated, or in other words, their pulsating nature is largely converted to a steady flow, by a pressure moderator 20 placed in a series with the peristaltic pump 16 and the catheter 14. As shown in FIG. 2, the moderator 20 includes a tube 22 lying within a chamber 24. The tube has an upper end 22u connected to the outlet 26 of the pump, and has a lower end 22l lying near the bottom of the chamber 24. The tube 22 is constructed of elastic material and is provided with slits 28 near its lower end. Whenever the pump 16 delivers a pulse of liquid through the tube 22, the increased pressure of the liquid separates the walls of the slits 28, and permits the liquid to pass out through the slits into the chamber 24. The upper end of the chamber 24 is filled with a gas 30 such as air, while the lower end of the chamber is filled with a column 32 of the liquid. Every pulse of liquid passing out of the tube through the slits 28 increases the height of the column 32 in the chamber, and compresses the gas 30 therein. The increased fluid pressure resulting from the increased pressure of the gas 30 and the slightly increased height of the column 32 causes the fluid to flow out of the bottom end of the chamber through an outlet 34. The outlet 34 is coupled through an intravenous filter and air eliminator 36 to the catheter 14. If the fluid is initially flowing into the patient slower than the desired rate (at which the pump is pumping fluid), then the pressure gradually increases at the outlet of the moderator, to flow fluid at a higher rate into the patient.

The moderator tube 22 is constructed of a thick-walled tube of elastic material such as silicon rubber. The tube 22 may have an outside diameter of about four millimeters, and a wall thickness of about one millimeter. When the pressure of fluid within the tube exceeds the pressure within the moderator chamber 24, by a predetermined amount, the walls of the slit spread apart, as shown at 28A in FIG. 3, to permit the escape of fluid through the slit into the chamber. The slit resists opening when the pressure in the tube 22 is only slightly higher than the pressure in chamber 24, such as less than the pressure of one foot of water. This prevents the uncontrolled flow of fluid from the container 10 through the pump 16 to the moderator chamber 24 when a pumping tube 40 in the pump is not squeezed closed. At a time after fluid is pumped from the moderator tube 22 into the moderator chamber 24, the pressure within the tube 22 will decrease to a level much lower than the pressure within the chamber 24. At that time, the considerable thickness of the elastic tube prevents the bending inwardly of the slit walls which would permit reverse flow of fluid for a moderate pressure difference. It may be noted that the moderator is provided with a pressure relief valve 38 connected to the upper portion of the chamber, to permit the escape of compressed gas if the pressure in the chamber exceeds a predetermined level such as 10 psig (about 500 mm Hg). This is to avoid excessive pressure in the event that the patient's blood vessel is occluded.

The peristaltic pump 16 includes a pumping tube 40 lying within a pump chamber 42. An air inlet 44 of the chamber housing delivers pulses of air, indicated at 46, with each pulse compressing the tube as to the configuration shown at 40A to expel fluid lying within the tube. A check valve 47 lying between the inlet of the pump at 48 and the container, allows the pumped fluid to flow only in a downward direction towards the pressure moderator. When a considerable pressure such as 30 psi is applied to the tube 40, the tube is fully collapsed to assure that all fluid is expelled from it. When the air pressure pulse is ended, the tube 40 can expand again to refill with fluid from the container 10.

The pressure of the fluid applied by the container 10 to the pump tube 40, depends upon the height of the fluid in the container and the adequacy of bubbling of air into the region above the fluid therein, as well as the height of the container above the pump; the pressure is typically about one foot of water (which is about one-half psig). If the flexible pump tube 40 were constructed of an elastic material such as silicon rubber, it would tend to expand too rapidly refill with fluid when the pressure pulse was removed. However, the tube could bulge outwardly in an unknown amount, depending upon the exact minimum pressure in the pump chamber 42 and the height of the fluid column above the pump. Any unknown amount of bulging affects the amount of fluid which is pumped in each cycle of operation of the pump, and therefore is undesirable where accurate control of the amount of fluid pumped towards the patient is desired. To avoid this, the pump tube 40 is constructed of a flexible but substantially inelastic material such as a polycarbonate plastic. The tube material can be at least translucent to permit monitoring of operation of the device.

While the use of a flexible but substantially nonelastic pump tube 40 prevents appreciable unpredictable bulging of the tube, it also has the disadvantage that the pump tube does not expand and refill with fluid as rapidly as could occur if a highly resilient pump tube were utilized. Of course, the filling of the tube to less than its full capacity is as desirable as filling it beyond the predetermined amount, in assuring accurately controlled delivery of fluid to the patient. To prevent this, the air input delivered through the inlet 44 includes a vacuum indicated at 52, of a level such as −9 psig after each positive pressure pulse 46 of a level such as 30 psig.

The controller 18 which applies the pressure and vacuum pulses to the pump, includes a pipe 54 which is connected to a moderate pressure supply such as a typical 50 psi air supply that is readily available in medical facilities. The high pressure air flows through a pressure reducer and valve 66 which is cycled to open and close to deliver the pressure pulses of about 30 psig to the pump inlet 44. The compressed air delivered through the pipe 54 is also delivered through a venturi device 58, so that a vacuum can be obtained from the throat of the venturi for delivery to the pump inlet 44 when a high pressure pulse is not being delivered thereto. The pneumatic valve 56 is opened and closed by a solenoid 60 which is operated by a low frequency voltage controlled oscillator 62, whose frequency can be varied to control the rate at which liquid is delivered to the patient. A simple oscillator 62 can be constructed which is operated by a battery, to avoid the use of the high voltages of wall outlets and the corresponding necessity for safeguards to prevent shocks to patients. Since the oscillator 62 delivers very little power, it can be operated for a long period of time with a small battery. A counter 64 is provided, to indicate the number of pulses which have been delivered, and therefore the amount of fluid that has been pumped to the patient. If, for example every compression of the pump tube causes the pumping of one milliliter, then the count displayed by the counter 64 indicates the number of milliliters of liquid that has been delivered to the patient since the counter was reset.

Thus, the invention provides a system for closely controlling the administration of fluid into a patient, which utilizes relatively simple and inexpensive disposable and sterile parts, which permits close control of the amount of administered fluid to the patient, and which assures that the fluid is applied in a relatively even stream to the patient. This is accomplished by a system which includes a peristaltic pump for pumping fluid out of a container, and a pressure moderator connected between the outlet of the pump and a catheter which leads to the patient to provide an even flow of fluid to the patient. The moderator can be formed of a tube of elastic material with a closed end lying at the lower end of the moderator chamber, and with slits in the closed end. Pulses of fluid exit through the slit into the chamber, to increase the height of the fluid column of the chamber and to compress gas lying at the upper portion of the chamber, so as to increase the pressure at which the fluid is pumped into the patient. The peristaltic pump can be constructed with a flexible tube that is compressed by pressure pulses, wherein the tube is constructed of non-elastic material to prevent its enlargement past a predetermined configuration, so as to control the amount of fluid pumped in each cycle of operation. A source for powering the pump applies pressure pulses to collapse the pump tube, and with each pulse being followed by a vacuum pulse that assures full expansion of the substantially nonelastic tube to draw in liquid.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. Apparatus for transferring a fluid from a container to a patient-connected catheter, in a controlled and primarily steady flow, comprising:
   a peristaltic pump having an inlet connectable to said container and a pump outlet; and
   a pressure moderator having an inlet coupled to said pump outlet and having a moderator outlet connectable to said patient-connected catheter;
   said moderator including walls forming a closed chamber connected to said outlet, and containing a quantity of said fluid and a gas, said chamber having a lower end connectable to said catheter, so that the fluid flowing to the patient passes first through said chamber and forms a fluid column of variable height therein, and including a flexible tube having an open end coupled to said pump outlet and a closed end said tube including a portion lying with said chamber and having at least one slit therein to permit the release of fluid into said chamber at each pulse of said peristaltic pump.

2. The apparatus described in claim 1 wherein:
   said flexible tube is constructed with walls thick and stiff enough to prevent opening until the pressure in said flexible tube exceeds the pressure in said chamber by at least the pressure of one foot of water.

3. A method for pumping fluid from a container containing fluid at close to ambient pressure to a patient, comprising:
   coupling said container through a check valve to a flexible tube;
   applying pressure pulses to the outside of said tube, to collapse said tube with each pulse; and
   passing fluid in pulses from said tube through a slit in an elastic tube into a moderator chamber containing gas and fluid and having an outlet, and passing fluid in an even flow out of said outlet.

4. In an apparatus for delivering fluid in a relatively even flow to a patient, which includes a peristaltic pump that pumps fluid in pulses, the improvement comprising:
   walls forming a moderator chamber with an inlet, and with an outlet connectable to a patient; and
   a flexible tube connected to said pump and having at least a portion lying in said chamber, said tube portion in said chamber having a slit therein so that pulses of fluid from said pump, can pass through said slit into said chamber, said chamber having a much greater volume than said tube to accumulate fluid therein.

* * * * *